United States Patent
Long et al.

(10) Patent No.: US 11,754,063 B2
(45) Date of Patent: Sep. 12, 2023

(54) NEGATIVE PRESSURE WOUND THERAPY DEVICE WITH SILENT PIEZOELECTRIC PUMP

(71) Applicant: KCI LICENSING, INC., San Antonio, TX (US)

(72) Inventors: Justin A. Long, Bournemouth (GB); Christopher B. Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 450 days.

(21) Appl. No.: 16/957,679

(22) PCT Filed: Dec. 18, 2018

(86) PCT No.: PCT/US2018/066161
§ 371 (c)(1),
(2) Date: Jun. 24, 2020

(87) PCT Pub. No.: WO2019/135900
PCT Pub. Date: Jul. 11, 2019

(65) Prior Publication Data
US 2021/0060216 A1   Mar. 4, 2021

Related U.S. Application Data

(60) Provisional application No. 62/612,900, filed on Jan. 2, 2018.

(51) Int. Cl.
*A61M 1/00* (2006.01)
*F04B 43/00* (2006.01)
*F04B 43/04* (2006.01)

(52) U.S. Cl.
CPC ........... *F04B 43/0081* (2013.01); *A61M 1/74* (2021.05); *A61M 1/82* (2021.05); *A61M 1/91* (2021.05);
(Continued)

(58) Field of Classification Search
CPC .. A61M 1/74; A61M 2205/3344; A61M 1/73; A61M 1/75; F04B 43/0081;
(Continued)

(56) References Cited

U.S. PATENT DOCUMENTS

| | | |
|---|---|---|
| 1,355,846 A | 10/1920 | Rannells |
| 2,547,758 A | 4/1951 | Keeling |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

International Search Report and Written Opinion in International Application No. PCT/US2018/066161, dated Apr. 2, 2019.

(Continued)

*Primary Examiner* — Guy K Townsend
*Assistant Examiner* — Seth Han

(57) ABSTRACT

A negative pressure wound therapy device includes at least one piezoelectric pump and a control circuit. The control circuit is configured to generate a first control signal to control operation of the at least one piezoelectric pump, the control signal having a first root mean square (RMS) voltage, transmit the first control signal to the at least one piezoelectric pump, identify at least one of a change of state of the at least one piezoelectric pump or an expiration of a duration of time associated with operation of the at least one piezoelectric pump, responsive to identifying the at least one of the change of state or the expiration of the duration of time, generate a second control signal having a second RMS voltage less than the first RMS voltage, and transmit the second control signal to the at least one piezoelectric pump.

14 Claims, 8 Drawing Sheets

(52) U.S. Cl.
CPC .............. *A61M 1/96* (2021.05); *F04B 43/046* (2013.01); *A61M 1/966* (2021.05); *A61M 2205/0294* (2013.01); *A61M 2205/3344* (2013.01); *A61M 2205/3368* (2013.01); *A61M 2205/502* (2013.01); *A61M 2205/52* (2013.01); *A61M 2205/581* (2013.01); *A61M 2205/582* (2013.01); *A61M 2205/583* (2013.01)

(58) Field of Classification Search
CPC ............ F04B 17/003; F04B 2201/0801; F04B 2201/0806; F04B 2203/0405; F04B 2203/00; F04B 2201/00; F04B 43/046; F04B 49/06; F04B 43/095
See application file for complete search history.

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 8,371,829 B2 | 2/2013 | Jaeb et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0219288 A1* | 10/2005 | Vogeley ................ F04B 43/046 347/10 |
| 2007/0242427 A1* | 10/2007 | Yamamoto .............. G06F 1/206 361/689 |
| 2008/0200857 A1* | 8/2008 | Lawhorn ................ G08B 19/00 602/41 |
| 2010/0310382 A1* | 12/2010 | Kidd .................... F04D 15/0088 417/44.1 |
| 2011/0054810 A1* | 3/2011 | Turner .................. A61M 1/784 702/47 |
| 2012/0016323 A1* | 1/2012 | Robinson ............ A61F 13/0216 604/319 |
| 2012/0046674 A1* | 2/2012 | Augarten .............. A61F 5/0059 606/151 |
| 2012/0109083 A1* | 5/2012 | Coulthard ............. A61M 1/962 604/319 |
| 2012/0259299 A1* | 10/2012 | Ryu ....................... A61M 1/96 604/319 |
| 2013/0209279 A1* | 8/2013 | Locke .................... F04B 53/08 417/313 |
| 2014/0017093 A1* | 1/2014 | Locke ................... F04B 19/006 417/32 |
| 2015/0250931 A1* | 9/2015 | Bharti ..................... A61M 1/82 604/319 |
| 2017/0143878 A1* | 5/2017 | Tanaka .................... A61M 1/74 |
| 2017/0298924 A1* | 10/2017 | Chen ..................... F04B 49/08 |
| 2017/0368239 A1* | 12/2017 | Askem .................. A61M 1/732 |

(56) References Cited

U.S. PATENT DOCUMENTS

| | | | |
|---|---|---|---|
| 2018/0209415 A1* | 7/2018 | Zhang | F04B 17/05 |
| 2020/0276367 A1* | 9/2020 | Seddon | A61M 1/96 |

FOREIGN PATENT DOCUMENTS

| | | | |
|---|---|---|---|
| AU | 755496 B2 | 12/2002 | |
| CA | 2005436 A1 | 6/1990 | |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| KR | 970005552 B1 * | 4/1997 | ....... A61F 13/00068 |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | WO-2013/171585 A2 | 11/2013 | |
| WO | WO-2017/191149 A1 | 11/2017 | |

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture" Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 pages English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds" Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.

(56) References Cited

OTHER PUBLICATIONS

Selections from W. Meyer and V. Schmieden, Bier's Hyperemic Treatment in Surgery, Medicine, and the Specialties A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

* cited by examiner

NEGATIVE PRESSURE WOUND THERAPY DEVICE WITH SILENT PIEZOELECTRIC PUMP

CROSS-REFERENCE TO RELATED APPLICATIONS

This application claims the benefit of priority under 35 U.S.C. § 371 to international patent application number PCT/US2018/066161, filed on Dec. 18, 2018, which claims the benefit of priority to U.S. Provisional Application No. 62/612,900, filed on Jan. 2, 2018, which are incorporated herein by reference in their entireties.

BACKGROUND

The present disclosure relates generally to wound therapy systems and devices, and more particularly to a negative pressure wound therapy device.

Negative pressure wound therapy (NPWT) is a type of wound therapy that involves applying negative pressure (relative to atmosphere pressure) to a wound site to promote wound healing. Some NPWT systems include a pump which operates to maintain the wound site at negative pressure by removing wound exudate from the wound site.

In some existing NPWT systems, a piezoelectric pump is used to apply the negative pressure to the wound site. Piezoelectric pumps can operate at very low noise levels (e.g., silently), which can reduce power requirements while also improving the perceived experience for a user. However, existing NPWT piezoelectric pumps are difficult to maintain in silent operation, due to thermal loading and other inefficiencies that development over the course of use.

In many existing NPWT systems, the leak tolerance of the system, and thus an associated alarm threshold, is determined by the capacity of the pump to maintain pressure with a leak. The battery capacity and life expectations also affect the system operation. These factors relate to the energy efficiency of the system. Piezoelectric pumps intended to operate silently may have decreasing energy efficiency as their thermal loading or required duty cycle goes up, reducing the ability of the NPWT systems to provide desired functionality.

SUMMARY

One implementation of the present disclosure is a negative pressure wound therapy (NPWT) device. The NPWT device includes at least one piezoelectric pump configured to apply a vacuum to a wound site, and a control circuit. The control circuit is configured to generate a first control signal to control operation of the at least one piezoelectric pump, the control signal having a first root mean square (RMS) voltage, transmit the first control signal to the at least one piezoelectric pump, identify at least one of a change of state of the at least one piezoelectric pump or an expiration of a duration of time associated with operation of the at least one piezoelectric pump, responsive to identifying the at least one of the change of state or the expiration of the duration of time, generate a second control signal having a second RMS voltage less than the first RMS voltage, and transmit the second control signal to the at least one piezoelectric pump.

In some embodiments, the NPWT device includes a temperature sensor configured to detect a first temperature of the at least one piezoelectric pump and output the first temperature to the control circuit. The control circuit identifies the change of state responsive to comparing the first temperature to a first temperature threshold and determining that the first temperature is greater than the first temperature threshold. In some embodiments, the control circuit is further configured to receive a second temperature of the at least one piezoelectric pump detected by the temperature sensor subsequent to transmission of the second control signal, compare the second temperature to a second temperature threshold less than or equal to the first temperature threshold, and responsive to the second temperature being less than the second temperature threshold, transmit a third control signal to the at least one piezoelectric pump, the third control signal having a third RMS voltage equal to the first RMS voltage.

In some embodiments, the at least one of the change of state or the expiration of the duration of time is associated with overheating of the at least one piezoelectric pump.

In some embodiments, the control circuit resets the timer responsive to transmitting the second control signal.

In some embodiments, the NPWT device includes a resonance detector configured to detect a first resonance frequency of the at least one piezoelectric pump and output the first resonance frequency to the control circuit. The control circuit identifies the change of state based on the first resonance frequency.

In some embodiments, the NPWT device includes a pressure sensor configured to detect a first pressure of at least one of the piezoelectric pump or the wound site and output the first pressure to the control circuit. The control circuit identifies the change of state responsive to comparing the first pressure to a target pressure and determining that the first pressure is greater than or equal to the target pressure. In some embodiments, the control circuit is further configured to count a number of identifications of the at least one of the change of state or the expiration of the duration of time while the first pressure is less than the target pressure, compare the count to a count threshold, and responsive to determining that the count is greater than the count threshold, output a notification including at least one of a visual output or an audible output.

In some embodiments, the control circuit is coupled to the piezoelectric pump by an alternating current circuit having a first arm and a second arm, and the control circuit is configured to generate the first control signal to have the first RMS voltage by modulating a first phase angle of a first signal component associated with the first arm relative to a second phase angle of a second signal component associated with the second arm.

In some embodiments, the control circuit generates the control signals as sine waves.

In some embodiments, the at least one piezoelectric pump includes at least a first piezoelectric pump and a second piezoelectric pump. Responsive to identifying the at least one of the change of state or the expiration of the duration of time, the control circuit transmits the second control signal to the first piezoelectric pump and transmits a third control signal having a third RMS voltage equal to the first RMS voltage to the second piezoelectric pump.

In some embodiments, the at least one piezoelectric pump is attached to a heat sink configured to dissipate heat from the at least one piezoelectric pump.

Another implementation of the present disclosure is a method. The method includes generating a first control signal having a first root mean square (RMS) voltage, transmitting the first control signal to at least one piezoelectric pump configured to apply a vacuum to a wound site, identifying at least one of a change of state of the at least one piezoelectric pump or an expiration of a duration of time associated with operation of the at least one piezoelectric pump, responsive to identifying the at least one of the change of state or the expiration of the duration of time, generating a second control signal having a second RMS voltage less than the first RMS voltage, and transmitting the second control signal to the at least one piezoelectric pump.

In some embodiments, the method includes receiving a first temperature of the at least one piezoelectric pump, wherein identifying the change includes comparing the first temperature to a first temperature threshold and determining that the first temperature is greater than the first temperature threshold.

In some embodiments, the method includes receiving a first temperature of the at least one piezoelectric pump, wherein identifying the change includes comparing the first temperature to a first temperature threshold and determining that the first temperature is greater than the first temperature threshold.

In some embodiments, the method includes initiating a timer responsive to transmitting the first control signal, and identifying the expiration of the duration of time using the timer.

In some embodiments, the method includes receiving a first resonance frequency of the at least one piezoelectric pump from a resonance detector and identifying the change of state based on the first resonance frequency.

In some embodiments, the method includes generating the first control signal to have the first RMS voltage by modulating a first phase angle of a first signal component associated with a first arm of an alternating current circuit coupled to the at least one piezoelectric pump relative to a second phase angle of a second signal component associated with a second arm of the alternating current circuit.

Another implementation of the present disclosure is a non-transitory computer readable medium storing computer executable instructions which when executed by a control circuit cause the control circuit to perform a method. The method includes generating a first control signal having a first root mean square (RMS) voltage, transmitting the first control signal to at least one piezoelectric pump configured to apply a vacuum to a wound site, identifying at least one of a change of state of the at least one piezoelectric pump or an expiration of a duration of time associated with operation of the at least one piezoelectric pump, responsive to identifying the at least one of the change of state or the expiration of the duration of time, generating a second control signal having a second RMS voltage less than the first RMS voltage, and transmitting the second control signal to the at least one piezoelectric pump.

In some embodiments, the method includes receiving a first temperature of the at least one piezoelectric pump, wherein identifying the change includes comparing the first temperature to a first temperature threshold and determining that the first temperature is greater than the first temperature threshold.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Referring generally to the FIGURES, a negative pressure wound therapy (NPWT) device and components thereof are shown, according to various exemplary embodiments. The NPWT device may include at least one piezoelectric pump and a control circuit. The at least one piezoelectric pump can be configured to apply a vacuum to a wound site. The control circuit can be configured to generate a first control signal to control operation of the at least one piezoelectric pump, the first control signal having a first root mean square (RMS) voltage. The control circuit can transmit the first control signal to the at least one piezoelectric pump. The control circuit can identify at least one of a change of state of the at least one piezoelectric pump or an expiration of a duration of time associated with operation of the at least one piezoelectric pump. Responsive to identifying the at least one of the change of state or the expiration of the duration of time, the control circuit can generate a second control signal having a second RMS voltage less than the first RMS voltage. The control circuit can transmit the second control signal to the at least one piezoelectric pump.

In some embodiments, the change of state and/or the expiration of the duration of time can indicate that the at least one piezoelectric pump has exceeded a temperature threshold or is susceptible to exceeding a temperature threshold, and thus may be susceptible to malfunctions, such as no longer running silently, or no longer applying a desired pressure to the wound site. The change of state may be associated with parameters such as temperatures of the NPWT device, a resonance frequency of the at least one piezoelectric pump, or the pressure applied to the wound site. By modifying operation of the at least one piezoelectric pump responsive to identifying the change of state and/or the expiration of the duration of time, the control circuit can enable the NPWT device to maintain desired continuous or semi-continuous operation.

In some embodiments, the control circuit generates and modulates the control signals in a manner which improves operation of the at least one piezoelectric pump, facilitating desired operation. For example, the control circuit can drive the control signals to have a sinusoidal waveform, which has smooth transitions between maximum and minimum values and thus may be most efficient in driving the at least one piezoelectric pump. The control circuit can modulate (e.g., ramp up, ramp down) the duty cycle of the at least one piezoelectric pump by changing phase angles between signal components applied to either arm of an alternating current circuit between the control circuit and the at least one piezoelectric pump. This can enable the control circuit to modulate the control signal relatively quickly, while reducing computational requirements for calculating parameters of the control signal.

Negative Pressure Wound Therapy System

Figure 1:
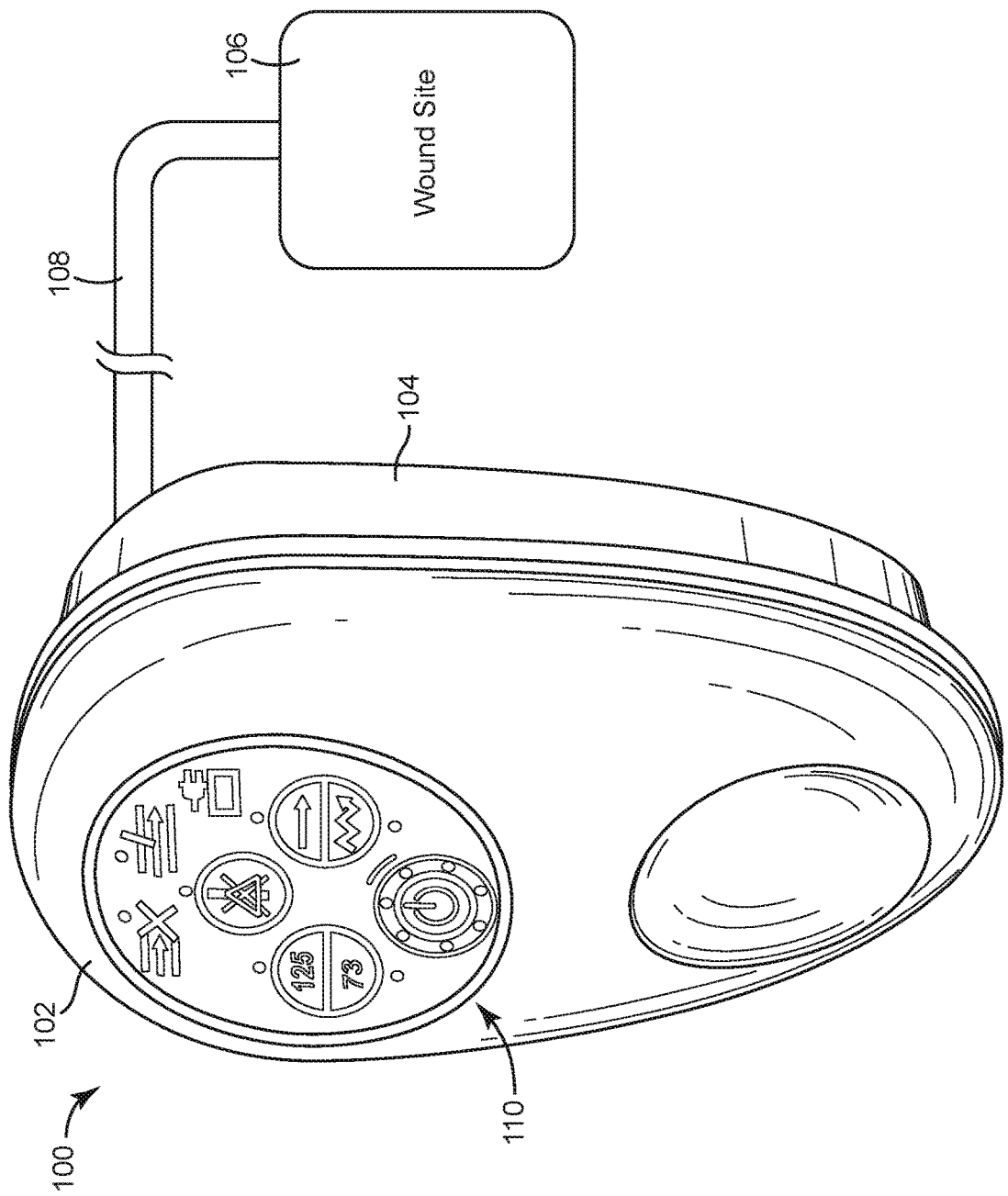
FIG. 1 is a drawing of a negative pressure wound therapy (NPWT) system including a NPWT device fluidly connected with a wound site, according to an exemplary embodiment.
Figure 2:
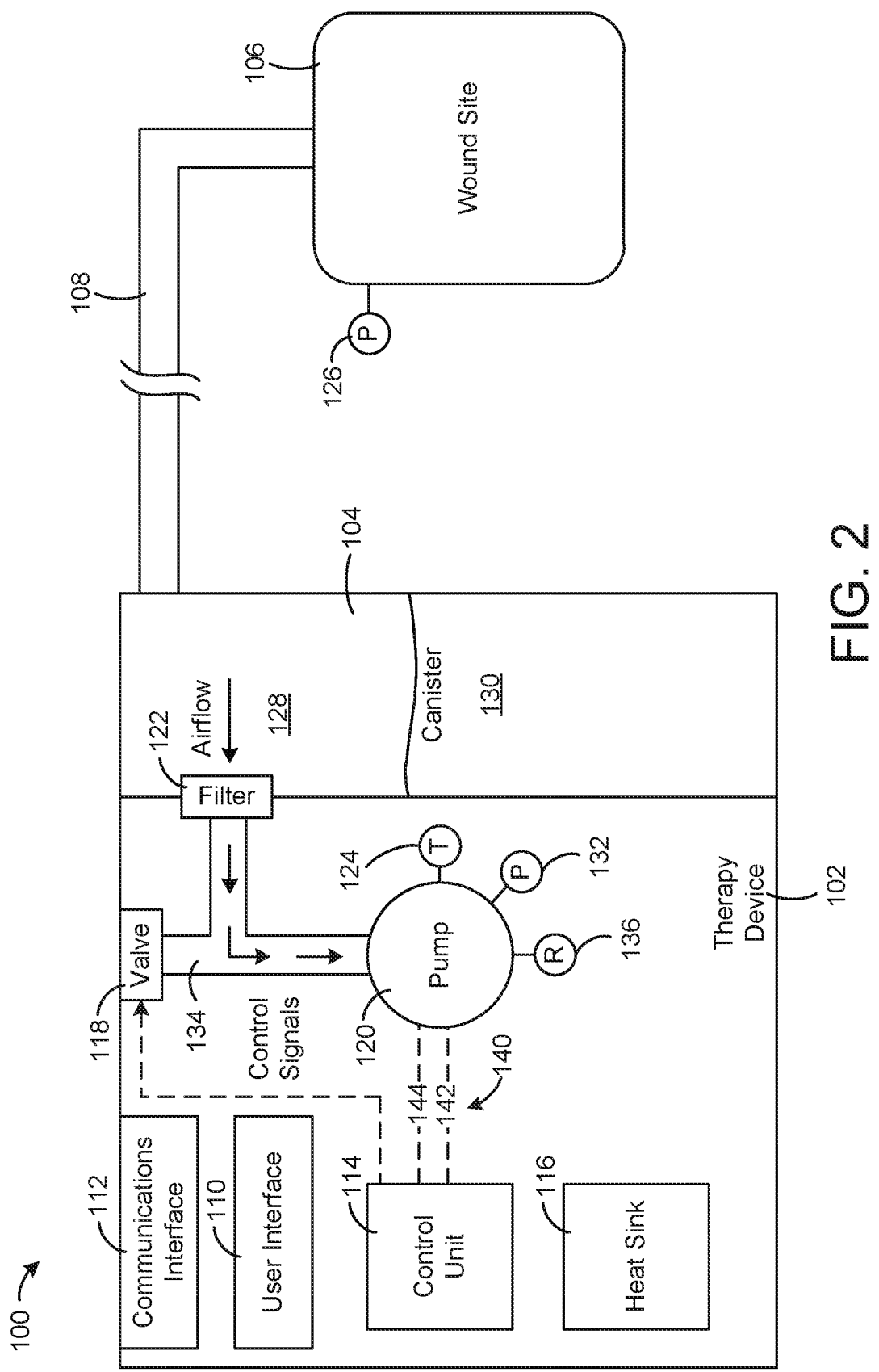
FIG. 2 is a block diagram illustrating the NPWT device of FIG. 1 in greater detail, according to an exemplary embodiment.

Referring now to FIGS. 1-2, a negative pressure wound therapy (NPWT) system 100 is shown, according to an exemplary embodiment. NPWT system 100 is shown to include a therapy device 102 fluidly connected to a wound site 106 via tubing 108. Wound site 106 may include a tissue wound as well as a wound dressing that covers the tissue wound and adheres to a patient's skin. Several examples of wound dressings which can be used in combination with NPWT system 100 are described in detail in U.S. Pat. No. 7,651,484 granted Jan. 26, 2010, U.S. Pat. No. 8,394,081 granted Mar. 12, 2013, and U.S. patent application Ser. No. 14/087,418 filed Nov. 22, 2013. The entire disclosure of each of these patents and patent applications is incorporated by reference herein.

Therapy device 102 can be configured to provide negative pressure wound therapy by reducing the pressure at wound site 106. Therapy device 102 can draw a vacuum at wound site 106 (relative to atmospheric pressure) by removing wound exudate, air, and other fluids from wound site 106. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from wound site 106 may include instillation fluid previously delivered to wound site 106. Instillation fluid can include, for example, a cleansing fluid, a prescribed fluid, a medicated fluid, an antibiotic fluid, or any other type of fluid which can be delivered to wound site 106 during wound treatment.

The fluids removed from wound site 106 pass through tubing 108 and are collected in canister 104, in some embodiments. Canister 104 may be a component of therapy device 102 configured to collect wound exudate and other fluids removed from wound site 106. In some embodiments, canister 104 is detachable from therapy device 102 to allow canister 104 to be emptied and replaced as needed. A lower portion 130 of canister 104 may be filled with wound exudate and other fluids removed from wound site 106, whereas an upper portion 128 of canister 104 may be filled with air. Therapy device 102 can be configured to draw a vacuum within canister 104 by pumping air out of canister 104. The reduced pressure within canister 104 can be translated to wound site 106 via tubing 108 such that wound site 106 is maintained at the same pressure as canister 104.

Referring particularly to FIG. 2, a block diagram illustrating therapy device 102 in greater detail is shown, according to an exemplary embodiment. Therapy device 102 is shown to include a pump 120, a filter 122, a valve 118, a heat sink 116, and a control unit 114. Pump 120 can be fluidly coupled to canister 104 (e.g., via conduit 134) and can be configured to draw a vacuum within canister 104 by pumping air out of canister 104. In some embodiments, pump 120 is configured to operate in both a forward direction and a reverse direction. For example, pump 120 can operate in the forward direction to pump air out of canister 104 and decrease the pressure within canister 104. Pump 120 can operate in the reverse direction to pump air into canister 104 and increase the pressure within canister 104. Pump 120 can be controlled by control unit 114, described in greater detail below.

Pump 120 is a piezoelectric pump. In some embodiments, the pump 120 includes a movable member (e.g., diaphragm) which undergoes mechanical displacement based on a voltage applied to the movable member, such as by oscillating in response to receiving an alternating current. By oscillating, the movable member can push air to generate the negative pressure applied by the pump 120. The movable member can be metallic. Pump 120 can include a copper disc with a slit which opens when pushed by the movable member. In some embodiments, the movable member oscillates at approximately 21 kHz. Under typical operational conditions, the pump 120 can operate silently or near silently. For example, noise generated by pump 120 can be less than a noise threshold which can be heard by a typical user. In an embodiment, pump 120 is a Vacuum Pump manufactured by Koge Micro Tech Co., Ltd.

In some embodiments, NPWT system 100 includes a plurality of pumps 120. For example, therapy device 102 may include multiple pumps 120, each coupled to tubing 108 and controlled by control unit 114. NPWT system 100 may include a plurality of therapy devices 102, each of which may include one or more pumps 120.

Filter 122 can be positioned between canister 104 and pump 120 (e.g., along conduit 134) such that the air pumped out of canister 104 passes through filter 122. Filter 122 can be configured to prevent liquid or solid particles from entering conduit 134 and reaching pump 120. Filter 122 may include, for example, a bacterial filter that is hydrophobic and/or lipophilic such that aqueous and/or oily liquids will bead on the surface of filter 122. Pump 120 can be configured to provide sufficient airflow through filter 122 that the pressure drop across filter 122 is not substantial (e.g., such that the pressure drop will not substantially interfere with the application of negative pressure to wound site 106 from therapy device 102).

Figure 3:
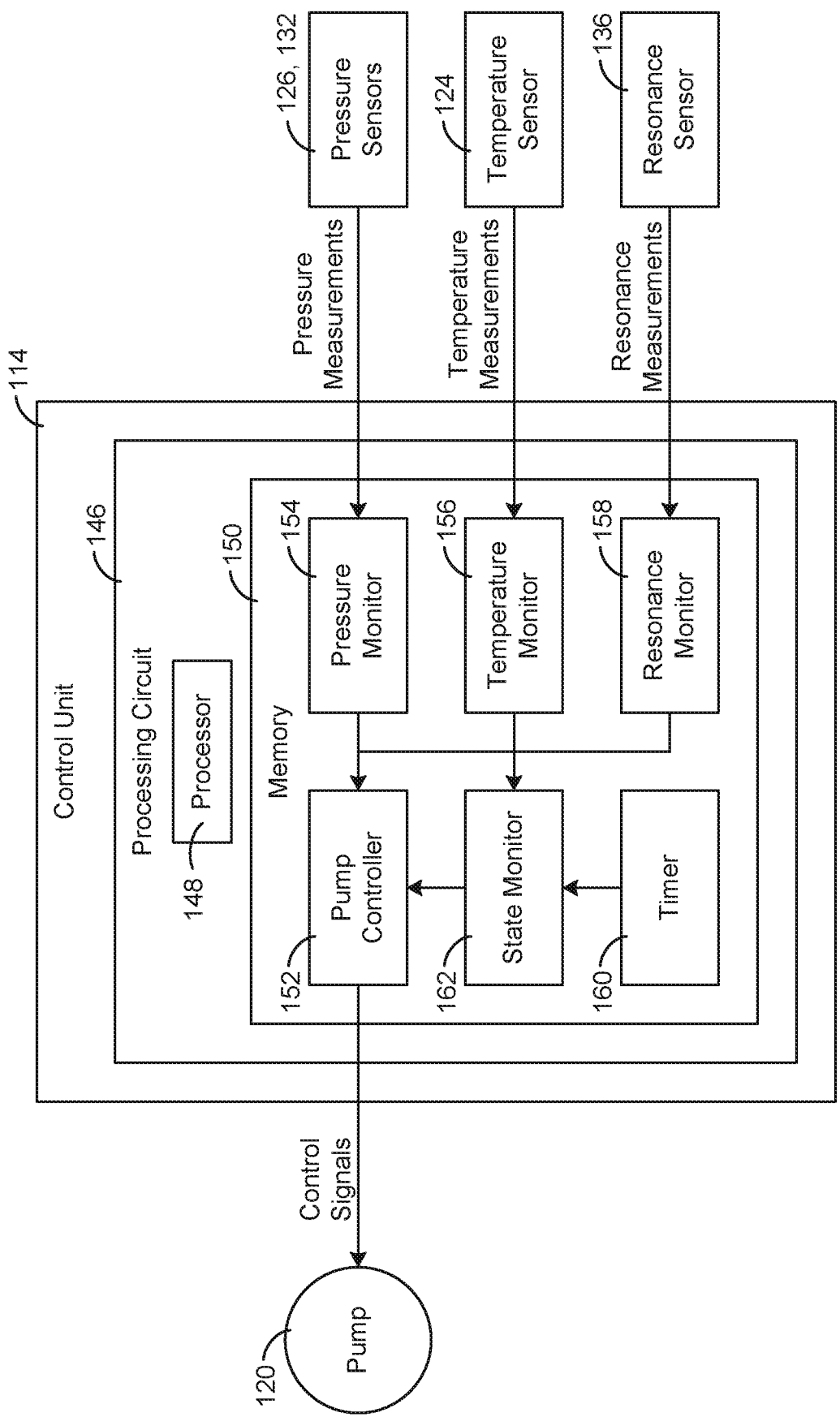
FIG. 3 is a block diagram of a control unit of the NPWT device of FIG. 1, according to an exemplary embodiment.

Valve 118 can be fluidly connected with pump 120 and filter 122 via conduit 134. In some embodiments, valve 118 is configured to control airflow between conduit 134 and the environment around therapy device 102. For example, valve 118 can be opened to allow airflow between conduit 134 and the environment around therapy device 102, and closed to prevent airflow between conduit 134 and the environment around therapy device 102. Valve 118 can be opened and closed by control unit 114, described in greater detail below. When valve 118 is closed, pump 120 can draw a vacuum within conduit 134 and canister 104 by causing airflow through filter 122 in a first direction, as shown in FIG. 2. When valve 118 is open, airflow from the environment around therapy device 102 may enter conduit 134 and fill the vacuum within conduit 134 and canister 104. The airflow from conduit 134 into canister 104 may pass through filter 122 in a second direction, opposite the first direction, as shown in FIG. 3.

While FIG. 2 illustrates the use of the canister 104 and filter 122, it will be appreciated that in some embodiments, the therapy device 102 may not include either the canister 104 or the filter 122, such that the pump 120 may be directly coupled to the wound site 106 via the tubing 108.

Heat sink 116 may be provided to increase a rate of heat dissipation from therapy device 102 or components thereof, such as pump 120. For example, heat sink 116 can be configured to have a relatively greater coefficient for convective heat transfer than other components of therapy device 102, such as by having a relatively greater surface area to volume ratio. Heat sink 116 may be mounted to control unit 114, pump 120, or a circuit board (not shown) to which control unit 114 and/or pump 120 are mounted. In some embodiments, heat sink 116 includes a plurality of fins.

Control unit 114 can be configured to operate pump 120, valve 118, and/or other controllable components of therapy device 102. In some embodiments, control unit 114 is configured to operate pump 120 by transmitting a control signal to pump 120 via alternating current circuit 140, which includes first arm 142 and second arm 144. The arms 142, 144 may be associated with corresponding pump drive electrodes for pump 120.

In some embodiments, therapy device 102 includes a variety of sensors, which can communicate sensor measurements to control unit 114. For example, therapy device 102 is shown to include a temperature sensor 124 configured to measure a temperature of pump 120 and communicate the measured temperature of pump 120 to control unit 114. Temperature sensor 124 may be a thermocouple.

In some embodiments, NPWT system 100 includes a pressure sensor 126 configured to measure the pressure at wound site 106 and communicate the measured pressure to control unit 114. NPWT system 100 may also include a pressure sensor 132 configured to measure the pressure at the pump, and a resonance sensor 136 configured to measure a resonance of pump 120 (e.g., of the movable member of pump 120). Control unit 114 can use the sensor measurements as inputs to various control operations performed by control unit 114 (described in greater detail with reference to FIGS. 4-7).

In some embodiments, therapy device 102 includes a user interface 110. User interface 110 may include one or more buttons, dials, sliders, keys, or other input devices configured to receive input from a user. User interface 110 may also include one or more display devices (e.g., LEDs, LCD displays, etc.), speakers, tactile feedback devices, or other output devices configured to provide information to a user. In some embodiments, the pressure measurements recorded by pressure sensors 124-126 and the orientation measurements recorded by orientation sensor 132 are presented to a user via user interface 110. User interface 110 can also display alerts generated by control unit 114.

In some embodiments, therapy device 102 includes a data communications interface 112 (e.g., a USB port, a wireless transceiver, etc.) configured to receive and transmit data. Communications interface 112 may include wired or wireless communications interfaces (e.g., jacks, antennas, transmitters, receivers, transceivers, wire terminals, etc.) for conducting data communications external systems or devices. In various embodiments, the communications may be direct (e.g., local wired or wireless communications) or via a communications network (e.g., a WAN, the Internet, a cellular network, etc.). For example, communications interface 112 can include a USB port or an Ethernet card and port for sending and receiving data via an Ethernet-based communications link or network. In another example, communications interface 112 can include a Wi-Fi transceiver for communicating via a wireless communications network or cellular or mobile phone communications transceivers.

Control Unit

Figure 4:
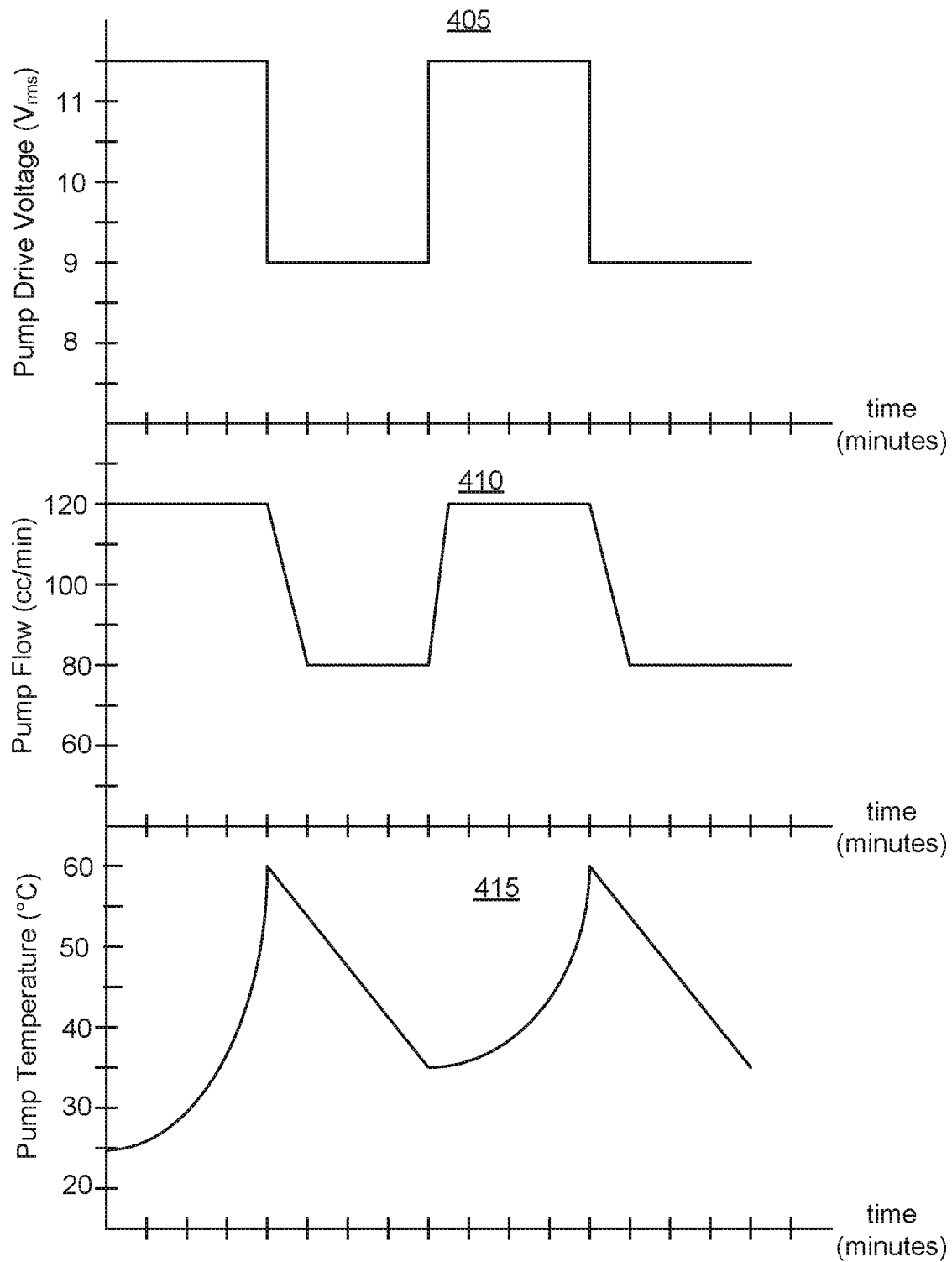
FIG. 4 is a schematic diagram of waveforms for controlling operation of a piezoelectric pump of an NPWT device, according to an exemplary embodiment.

Referring now to FIG. 4, a block diagram illustrating control unit 114 in greater detail is shown, according to an exemplary embodiment. Control unit 114 is shown to include a processing circuit 146 including a processor 148 and memory 150. Processor 148 may be a general purpose or specific purpose processor, an application specific integrated circuit (ASIC), one or more field programmable gate arrays (FPGAs), a group of processing components, or other suitable processing components. Processor 148 is configured to execute computer code or instructions stored in memory 150 or received from other computer readable media (e.g., CDROM, network storage, a remote server, etc.).

Memory 150 may include one or more devices (e.g., memory units, memory devices, storage devices, etc.) for storing data and/or computer code for completing and/or facilitating the various processes described in the present disclosure. Memory 150 may include random access memory (RAM), read-only memory (ROM), hard drive storage, temporary storage, non-volatile memory, flash memory, optical memory, or any other suitable memory for storing software objects and/or computer instructions. Memory 150 may include database components, object code components, script components, or any other type of information structure for supporting the various activities and information structures described in the present disclosure. Memory 150 may be communicably connected to processor 148 via processing circuit 146 and may include computer code for executing (e.g., by processor 148) one or more processes described herein. When processor 148 executes instructions stored in memory 150, processor 148 generally configures control unit 114 (and more particularly processing circuit 146) to complete such activities.

Control unit 114 is shown to include a pump controller 152. Pump controller 152 generates control signals to control operation of pump 120. Pump controller 152 can configure parameters of the control signals, such as current, voltage, frequency, amplitude, or intermittency. In some embodiments, pump controller 152 generates alternating current control signals having a root mean square (RMS) voltage, and transmits the control signals to pump 120 via alternating current circuit 140 (as shown in FIG. 3). For example, pump controller 152 can generate the control signals to have a particular RMS voltage by modulating a first phase angle of a first signal component associated with first arm 142 relative to a second phase angle of a second signal component associated with second arm 144.

As will be described with further reference to FIGS. 4-7, pump controller 152 can modulate the control signals to have specified waveforms. For example, pump controller 152 can modulate the control signals to have square, triangular, or sinusoidal waveforms. Square waveforms may result in thermal loading of pump 120 by oscillating between peak voltages of opposite signs, spending more time at peak voltage such that the transition between the peaks opposite signs is abrupt. Triangular waveforms may have reduced effectiveness by having amplitudes near the peaks for a relatively low fraction of the total waveform duration. In some embodiments, pump controller 152 can improve operation of pump 120 by modulating the control signals to have sinusoidal waveforms (see FIG. 5B), which provides smooth transitions between peaks and valleys, efficiently applying the alternating current signal to pump 120 while reducing the likelihood of undesired thermal loading. For example, it will be appreciated that the sinusoidal waveform can be smooth, as compared to the square waveform, which can include a step function transition from a minimum value to a maximum value (see FIG. 5A); or a triangular waveform, which can include a sharp corner where a slope of the waveform changes sign instantaneously or near instantaneously. In some embodiments, the sinusoidal waveform is based on a single sine (or cosine) wave function (as compared to a square waveform or triangular waveform, which may be generated by combining multiple sine wave functions of varying amplitudes). Pump controller 152 can modulate the sinusoidal control signals to have particular RMS voltages by modulating the first phase angle of the first sinusoidal signal component associated with first arm 142 relative to the second phase angle of the second sinusoidal signal component associated with second arm 144.

In some embodiments, pump controller 152 modulates voltage of the control signal by modulating a first phase angle of a first signal component associated with first arm 142 relative to a second phase angle of a second signal component associated with second arm 144. For example, pump controller 152 can initially output the control signal with the first phase angle being 180 degrees offset from the second phase angle, and increase the voltage by reducing the offset (e.g., reducing from 180 degrees towards 0 degrees). As such, pump controller 152 can more quickly achieve a desired voltage than by existing methods based on calculating voltage. In addition, pump controller 152 can reduce computational burden by changing the phase angle, which can avoid either (1) requiring multiply/divide capability or (2) re-programming memory each time amplitude is changed.

Control unit 114 is shown to include a pressure monitor 154. Pressure monitor 154 can be configured to monitor the pressure within pump 120 and/or the pressure at wound site 106 using feedback from pressure sensors 124-126. For example, pressure sensors 124-126 may provide pressure measurements to pressure monitor 152. Pressure monitor 152 can use the pressure measurements to determine the pressure within pump 120 and/or the pressure at wound site 106 in real-time. Pressure monitor 152 can provide the pressure value to state monitor 162 and/or pump controller 152 for use as an input to control processes performed by such components.

Control unit 114 can include a temperature monitor 156. Temperature monitor 156 can monitor the temperature of pump 120 using temperature measurements from temperature sensor 124, and use the temperature measurements to calculate the temperature of pump 120, in real-time. Similar to pressure monitor 154, temperature monitor 156 can provide the temperature of pump 120 to state monitor 162 and/or pump controller 152 for use as an input to control processes performed by such components.

In some embodiments, control unit 114 includes a resonance monitor 158. Resonance monitor 158 can receive resonance measurements from resonance sensor 136, and determine a resonance frequency of pump 120, in real-time. Similar to pressure monitor 154 and temperature monitor 156, resonance monitor 158 can transmit the determined resonance frequency to state monitor 162 and/or pump controller 152 for use as an input to control processes performed by such components.

Control unit 114 includes a timer 160, in some embodiments. Control unit 114 (or components thereof, such as pump controller 152) can initiate and/or reset timer 160 in response to various trigger conditions. For example, control unit 114 can initiate timer 160 responsive to pump controller 152 transmitting a control signal (e.g., a control signal having a first RMS voltage) to pump 120. Control unit 114 can reset timer 160 responsive to transmitting a control signal (e.g., a control signal having a second RMS voltage) to pump 120. Timer 160 can output a time to state monitor 162 and/or pump controller 152 for use as an input to control processes performed by such components.

In some embodiments, control unit 114 includes a state monitor 162. State monitor 162 can receive sensor measurements from sensors 124, 126, 132, 136 (e.g., via corresponding monitors 154, 156, 158), and execute operations using the received sensor measurements. State monitor 162 can also receive the time outputted by state monitor 162. In various embodiments, state monitor 162 is configured to determine whether a state of pump 120 indicates that pump 120 is overheating or may be susceptible to overheating, which can allow pump controller 152 to modify control of pump 120 before noise generation, overheating, or other undesired conditions of pump 120 occur.

State monitor 162 can identify at least one of a change of state of pump 120 or an expiration of a duration of time associated with operation of pump 120. In some embodiments, state monitor 162 identifies the change of state of pump 120 based on temperature. State monitor 162 can receive the temperature of pump 120 from temperature monitor 156. State monitor 162 can compare the temperature of pump 120 to a first temperature threshold, and identify the change of state responsive to the temperature of pump 120 being greater than the first temperature threshold. The first temperature threshold may be equal to (or slightly less) than a temperature at which pump 120 generates noise (e.g., whistling or other noise at a volume audible to a typical user), overheats, or loses efficiency. As such, identifying the change of state when the temperature is greater than the first temperature threshold can allow NPWT system 100 to take action to reduce thermal load on pump 120 before undesired operation occurs (or mitigate undesired operation before it is exacerbated by continued operation above the first temperature threshold). In some embodiments, the first temperature threshold is 63 degrees Celsius. The first temperature threshold can be greater than or equal to 50 degrees Celsius and less than or equal to 70 degrees Celsius. The first temperature threshold can be greater than or equal to 60 degrees Celsius and less than or equal to 65 degrees Celsius. It will be appreciated that the first temperature threshold may vary based on factors such as the composition, size, and/or drive voltage of pump 120.

State monitor 162 can also identify the change of state of pump 120 based on pressure. For example, state monitor 162 can receive the pressure of pump 120 and/or wound site 106 from pressure monitor 154. State monitor 162 can compare the pressure to a corresponding target pressure. The target pressure can be a desired pressure at which NPWT system 100 is properly applying a vacuum to wound site 106. State monitor 162 can identify the change of state responsive to determining that the pressure is greater than or equal to the target pressure (which can indicate that pump 120 need not necessarily be driven at the instant voltage, but rather may be temporarily be driven at a lower voltage to help prevent or mitigate overheating or other undesired operation). In some embodiments, the target pressure is 125 mmHg. The target pressure may be greater than or equal to 100 mmHg and less than or equal to 200 mmHg.

In some embodiments, state monitor 162 identifies the change of state of pump 120 based on resonance frequency. State monitor 162 can receive the resonance frequency of pump 120 from resonance monitor 158. State monitor 162 can compare the resonance frequency to a pump curve indicating a relationship between frequency and efficiency to determine whether an efficiency difference between an instant efficiency of pump 120 and a desired or maximum efficiency is greater than a threshold efficiency difference, and identify the change of state responsive to the efficiency difference being greater than the threshold efficiency difference.

State monitor 162 can identify the expiration of the duration of time based on receiving the time from the timer 160. For example, state monitor 162 can periodically receive the time from the timer 160, compare the time to a threshold duration of time, and identify the expiration of the duration of time based on the time exceeding the duration of time. The threshold duration of time can correspond to a time after which pump 120 may be expected to overheat or otherwise undergo undesired operation. In an embodiment, the threshold duration of time is 5 minutes. The threshold duration of time may be greater than or equal to 1 minute and less than or equal to 20 minutes. It will be appreciated that the threshold duration of time may vary based on various factors affecting the rate of heat generation, storage, and dissipation by pump 120, such as the composition, size, and/or drive voltage of pump 120.

In some embodiments, state monitor 162 outputs a notification associated with identifying the at least one of the change of state or the expiration of the duration of time. For example, state monitor 162 can cause user interface 110 to output at least one of a visual output or an audible output. In some embodiments, state monitor 162 counts a number of identifications of the at least one of the change of state or the expiration of the duration of time, compares the count to a count threshold, and responsive to determining that the count is greater than the count threshold, outputs the notification. The state monitor 162 may count the number of identifications while the pressure of at least one of pump 120 or wound site 106 is less than the corresponding target pressure, which may indicate that the pump 120 is overheating or susceptible to overheating without being able to achieve the target pressure.

In some embodiments, where NPWT system 100 includes a plurality of pumps 120, pump controller 152 (or a plurality of pump controllers 152 acting in unison) can control operation of the plurality of pumps 120. For example, pump controller 152 can drive a first pump of the plurality of pumps 120 at a first RMS voltage (e.g., a high or maximum RMS voltage), and drive at least one second pump 120 of the plurality of pumps 120 at a second RMS voltage less than the first RMS voltage. In response to identifying the at least one of the change of state of one or more pumps 120 or the expiration of the duration of time, pump controller 152 can generate a control signal to drive first pump 120 at a lower RMS voltage; pump controller 152 may also generate control signal(s) to drive one or more of the at least one second pump 120 at the first RMS voltage. As such, pump controller 152 can modify operation of the plurality of pumps 120 in order to maintain the target pressure at wound site 106 while avoid overheating or other undesired effects of operating each of the plurality of pumps 120.

Waveforms Generated by Control Unit for Driving Piezoelectric Pump

Referring now to FIG. 4 and further to FIGS. 2-3, a schematic diagram illustrating operational parameters of pump 120 when driven by a square wave control signal is shown, according to an exemplary embodiment. Pump 120 is shown to be driven by square wave control signal 405, with a maximum RMS voltage of 11 $V_{rms}$ for four minutes, alternating with a minimum RMS voltage of 9 $V_{rms}$ four minutes, in order to achieve a target pressure of 125 mmHg. The square wave control signal 405 causes pump 120 to deliver a flow rate 410 of 120 cc/min when driven at 11 $V_{rms}$ at the target pressure, then quickly reduce to a flow rate of 80 cc/min when driven at 9 $V_{rms}$, then quickly return to the flow rate of 120 cc/min. Notably, the continuous voltage at 11 $V_{rms}$ causes temperature 415 of pump 120 to quickly increase from approximately 25 degrees Celsius (e.g., room temperature) to almost 60 degrees Celsius (at which pump 120 may be susceptible to undesired effects from overheating). As shown in FIG. 4, the temperature 415 may not decrease during the first 9 $V_{rms}$ cycle all the way to the initial temperature, indicating heat storage in pump 120; while not illustrated in FIG. 4, the peak temperature 415 may continue to increase from cycle to cycle as pump 120 continues to store heat.

Figure 5A:
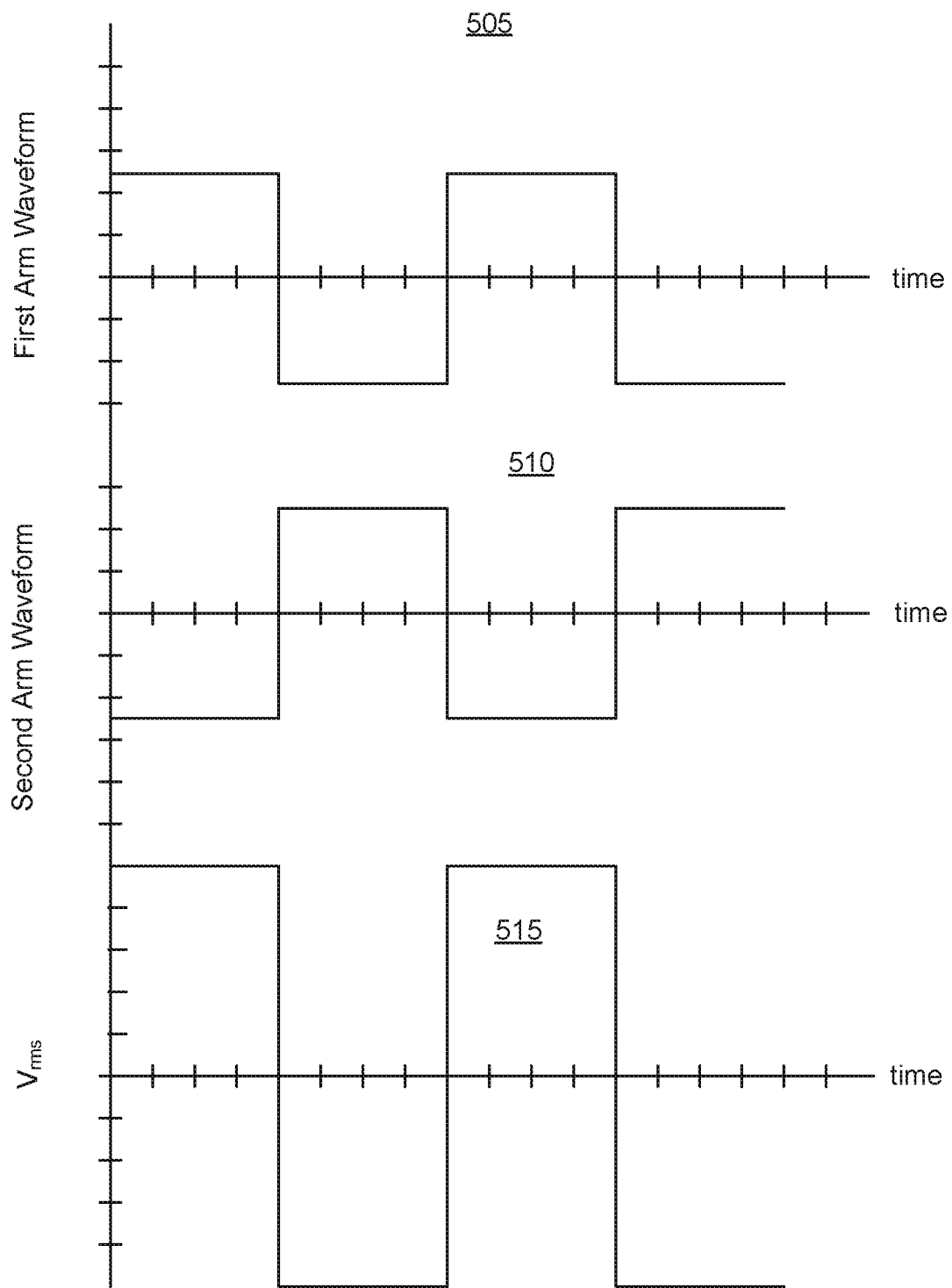
FIG. 5A is a schematic diagram of square wave alternating current circuit waveforms for modulating voltage of a control signal for controlling operation of a piezoelectric pump of an NPWT device, according to an exemplary embodiment.

Referring now to FIG. 5A and further to FIGS. 2-3, a schematic diagram illustrating alternating current control signals generated by pump controller 152 for driving pump 120 via alternating current circuit 140 is shown, according to an exemplary embodiment. As shown in FIG. 5A, a first arm waveform 505 may be driven with a phase angle difference of 180 degrees relative to a second arm waveform 510, resulting in an RMS voltage 515. In existing systems which rely on square wave signals as shown in FIG. 5A to drive pump 120, pump 120 may be susceptible to overheating, such as due to the sharp changes in direction of current between the waveforms 505, 510.

Figure 5B:
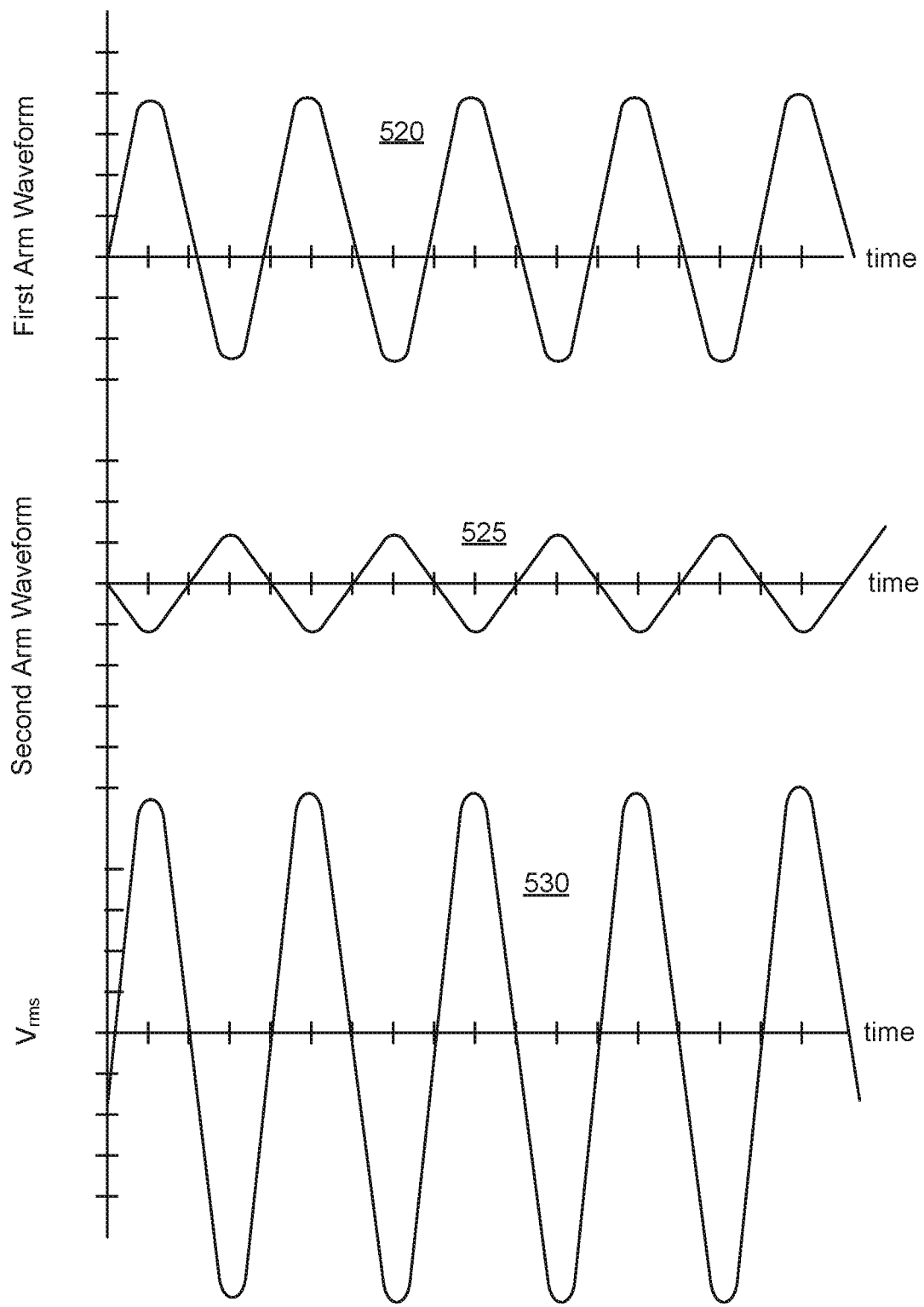
FIG. 5B is a schematic diagram of sine wave alternating current circuit waveforms for modulating voltage of a control signal for controlling operation of a piezoelectric pump of an NPWT device, according to an exemplary embodiment.

Referring now to FIG. 5B and further to FIGS. 2-3, another schematic diagram illustrating alternating current signals generated by pump controller 152 for driving pump 120 via alternating current circuit 140 is shown, according to an exemplary embodiment. As shown in FIG. 5B, a first arm waveform 520 may be driven with a phase angle difference of 180 degrees relative to a second arm waveform 525, resulting in an RMS voltage 530. The first arm waveform 520 and second arm waveform 525 are provided as sinusoidal signals (e.g., by using pump controller 152 to generate the control signals as sinusoidal signals). As compared to using the square wave-based signal of FIG. 5A, driving pump 120 using the sinusoidal signal of FIG. 5B can reduce the likelihood of overheating by reducing sharp changes in direction of current. In some embodiments, pump controller 152 generates the first arm waveform 520 using a first sine wave function, and generates the second arm waveform 525 using a second sine wave function having a desired phase angle difference as compared to the first arm waveform 520.

Figure 6:
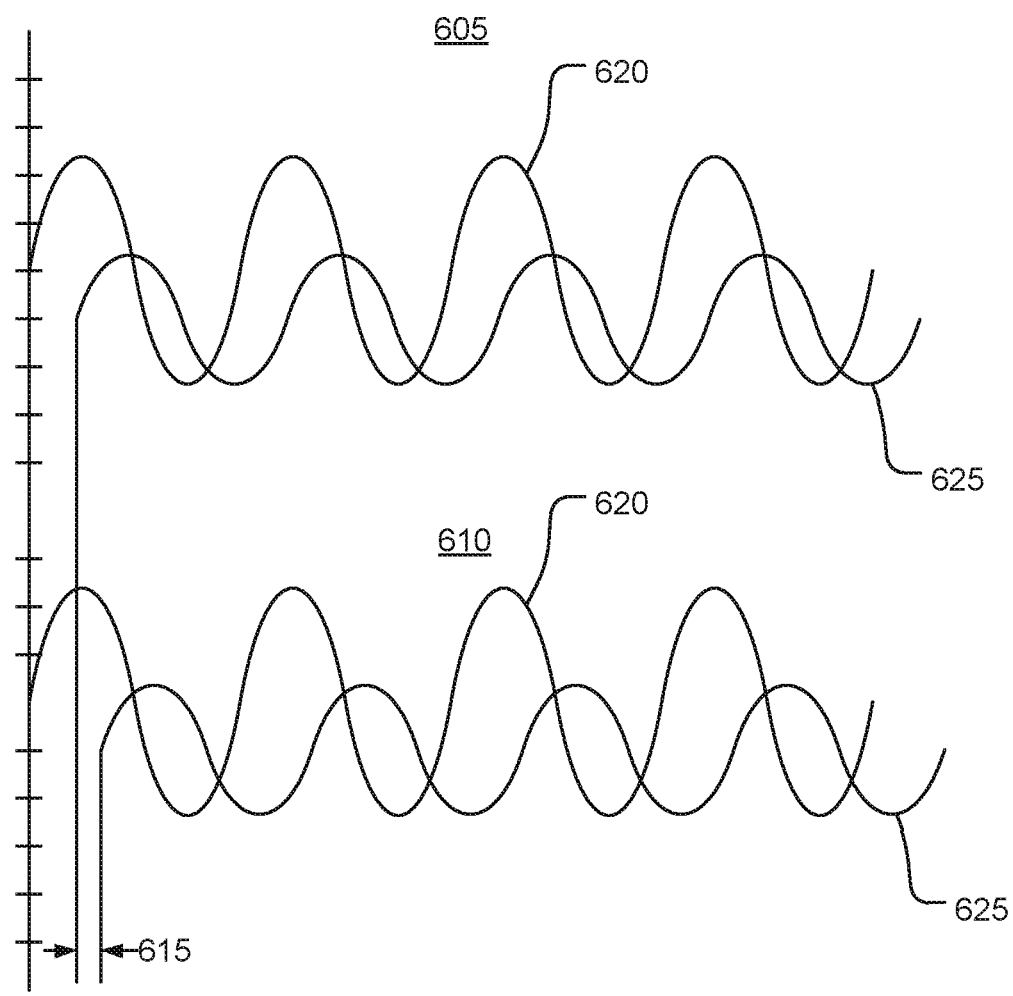
FIG. 6 is a schematic diagram of sinusoidal alternating current circuit waveforms for modulating voltage of a control signal for controlling operation of a piezoelectric pump of an NPWT device, according to an exemplary embodiment.

Referring now to FIG. 6 and further to FIGS. 2-3, a schematic diagram illustrating alternating current controls with sinusoidal waveforms generated by pump controller 152 for driving pump 120 via alternating circuit 140 is shown, according to an exemplary embodiment. As shown in FIG. 6, a first arm waveform 620 is offset from a second arm waveform 625. Pump controller 152 can modulate the resulting RMS voltage of the control signal by shifting the phase angle of second arm waveform 625 (or first arm waveform 620) by phase offset 615 to modulate the resulting RMS voltage. For example, shifting the phase angle of second arm waveform 625 by phase offset 615 can increase the resulting RMS voltage from 8 $V_{rms}$ to 11 $V_{rms}$.

Control Processes

Figure 7:
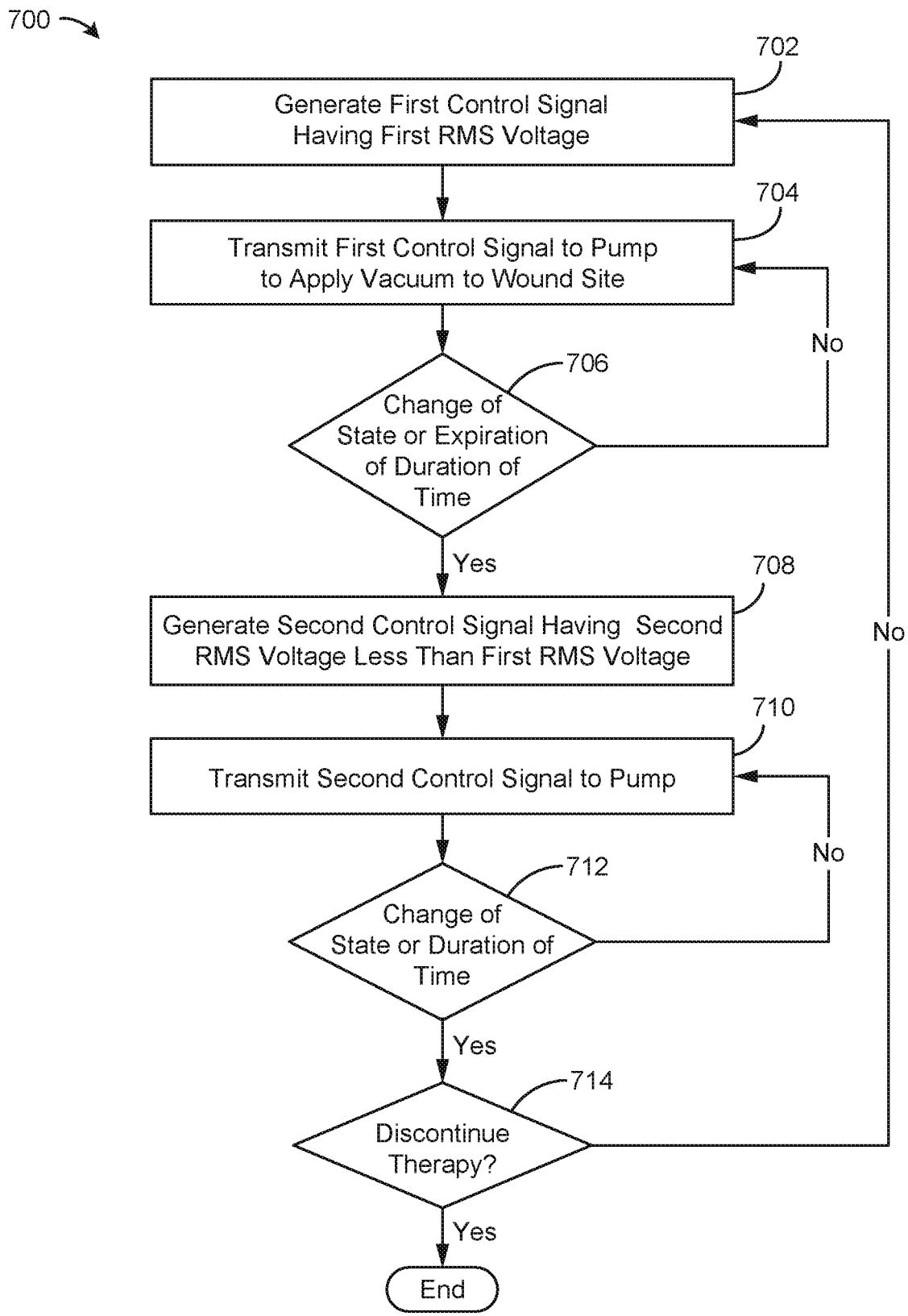
FIG. 7 is a flowchart of a process for operating the NPWT device of FIG. 1, according to an exemplary embodiment.

Referring now to FIG. 7, a flowchart of a process 700 for operating a negative pressure wound therapy (NPWT) device is shown, according to an exemplary embodiment. Process 700 can be performed by one or more components of NPWT system 100, as described with reference to FIGS. 1-6. For example, process 700 can be performed by therapy device 102 using control unit 114 to operate pump 120.

Process 700 is shown to include generating a first control signal having a first RMS voltage (step 702). The first control signal can be generated by generating a first signal component associated with a first arm of an alternating current circuit for driving a piezoelectric pump to have a first phase angle, and generating a second signal component associated with a second arm of the alternating current circuit for driving the piezoelectric pump to have a second phase angle. The amplitude of the control signal can be modulated by modulating the first phase angle relative to the second phase angle. In some embodiments, the first control signal is generated as a sinusoidal signal, such as by generating the first signal component based on a first sine wave function and the second signal component based on a second sine wave function having a desired phase difference relative to the first sine wave function.

Process 700 is shown to include transmitting the first control signal to a piezoelectric pump to apply a vacuum to a wound site (step 704). The first control signal can cause the piezoelectric pump to oscillate at a desired frequency, such that the piezoelectric pump draws a vacuum against the wound site. In various embodiments where the first control signal is a sinusoidal signal, heat generation by the piezoelectric pump can be reduced, such as due to the smooth transition between maximum and minimum values of the first control signal.

Process 700 is shown to include identifying at least one of a change of state of the piezoelectric pump or an expiration of a duration of time associated with operation of the piezoelectric pump (step 706). The identification can be used to avoid overheating or other undesired operational states of the piezoelectric pump.

In some embodiments, identifying the change of state includes identifying the change of state based on a temperature of the piezoelectric pump. For example, a temperature of the pump can be determined based on a temperature measurement received from a temperature sensor. The temperature of the pump can be compared to a first threshold. Responsive to determining that the first temperature is greater than the first temperature threshold, the change of state can be identified.

Identifying the change of state may include identifying the change of state based on a pressure of at least one of the pump or the wound site. For example, a pressure can be determined based on pressure measurements received from a pressure sensor at the pump and/or a pressure sensor at the wound site. The pressure can be compared to a target pressure, which may be associated with desired operation of the pump (e.g., desired vacuum at the wound site). Responsive to determining that the pressure is greater than the target pressure (e.g., in absolute value), the change of state can be identified. As such, if the pump is drawing a greater vacuum than the target pressure at the wound site, the change of state can be identified so that the pump may be driven at a lower voltage as described below.

Identifying the change of state may include identifying the change of state based on a resonance frequency of the pump. In some embodiments, a resonance frequency of the pump can be determined based on a frequency measurement from a frequency sensor. The change of state may be identified based on the resonance frequency being different from a target frequency by more than a threshold difference, which can indicate that the pump is operating away from a target efficiency, and may instead be converting electrical energy from the first control signal to heat rather than mechanical movement. In some embodiments, identifying the change of state includes retrieving a table of pump efficiency as a function of resonance frequency, and using the table to determine whether the resonance frequency differs from the target frequency.

In some embodiments, identifying the expiration of the duration of time is based on a timer. For example, the timer may be initiated responsive to transmitting the first control signal, which can indicate the start of operation of the pump at the first RMS voltage. The timer can be periodically outputted (or periodically polled), and compared to the duration of time. Responsive to the timer exceeding the duration of time, the expiration of the duration of time can be identified.

Process 700 is shown to include, responsive to identifying the at least one of the change of state or the expiration of the duration of time, generating a second control signal having a second RMS voltage less than the first RMS voltage (step 708). The second control signal can be generated by modulating the first phase angle of the first signal component associated with the first arm of the alternating current circuit relative to the second phase angle of the second signal component associated with the second arm of the alternating circuit current. In some embodiments, such as where the second control signal is generated responsive to identifying the expiration of the duration of time, the timer can be reset responsive to generating (or transmitting) the second control signal. If the at least one of the change of state or the expiration of the duration of time is not identified, then a control signal having the first RMS voltage may be continued to be applied to the pump.

Process 700 is shown to include transmitting the second control signal to the pump (step 710). By transmitting the second control signal having the second RMS voltage less than the first RMS voltage to the pump, overheating of the pump can be avoided. In some embodiments, a number of identifications of the at least one of the change of state or the expiration of the duration of time can be counted. The count can be compared to a count threshold. Responsive to determining that the count is greater than the count threshold, at least one of a visual output or an audible output can be outputted, such as to provide a notification of malfunction of the pump. In some embodiments, the count is incremented while the first pressure is less than the target pressure, so that the notification is provided based on the pump being unable to achieve the target pressure.

Process 700 is shown to include identifying an additional at least one of a change of state or expiration of a duration of time (712). The additional at least one of the change of state or the expiration of the duration of time may indicate that the operational mode of the second control signal (e.g., driving the pump at a lower RMS voltage) may be discontinued and/or the operational mode of the first control signal (e.g., driving the pump at a higher RMS voltage) may be reinstated. If the additional at least one of the change of state or duration of time is not identified, then the second control signal may be continued to be transmitted to the pump.

Responsive to identifying the additional at least one of the change of state or duration of time, process 700 is shown to include determining whether therapy is to be discontinued (714). For example, the determination may be performed based on a user input indicating instructions to discontinue therapy, or detection of a wound condition or dressing condition indicating therapy is to be discontinued. If therapy is not to be discontinued, then process 700 may be continued, such as by generating and transmitting the first control signal (e.g., to reinstate an operational mode using a relatively higher RMS voltage). Responsive to determining that therapy is to be discontinued, process 700 may be terminated, such as by discontinuing control signal transmission to the pump (or transmitting a control signal having a nominal or zero voltage to the pump).

In some embodiments, a second temperature of the pump can be received subsequent to transmission of the second control signal. The second temperature can be compared to a second threshold that is less than or equal to the first temperature threshold. In response to determining that the second temperature is less than the second temperature threshold, a third control signal can be generated and transmitted to the pump, the third control signal having a third RMS voltage greater than the second RMS voltage (e.g., equal to the first RMS voltage). As such, when the pump has cooled down to a temperature less than the second temperature threshold, the amplitude of the control signal used to drive the pump can be increased to increase performance by the pump. It will be appreciated that the first and second temperature thresholds may be used together, such that the pump can be driven cyclically between high voltage and low voltage states to maintain performance at a relatively high level while avoiding overheating.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A negative pressure wound therapy device, comprising:
at least one piezoelectric pump configured to apply a vacuum to a wound site;
a heat sink attached to the at least one piezoelectric pump and configured to dissipate heat from the at least one piezoelectric pump
a control circuit configured to:
generate a first control signal to control operation of the at least one piezoelectric pump, the control signal having a first root mean square (RMS) voltage;
transmit the first control signal to the at least one piezoelectric pump;
identify at least one of a change of state of the at least one piezoelectric pump or an expiration of a duration of time associated with operation of the at least one piezoelectric pump;
responsive to identifying the at least one of the change of state or the expiration of the duration of time, generate a second control signal having a non-zero second RMS voltage less than the first RMS voltage; and
transmit the second control signal to the at least one piezoelectric pump;
a temperature sensor configured to detect a first temperature of the at least one piezoelectric pump and output the first temperature to the control circuit, wherein the control circuit identifies the change of state responsive to comparing the first temperature to a first temperature threshold and determining that the first temperature is greater than the first temperature threshold; and
a resonance detector configured to detect a first resonance frequency of the at least one piezoelectric pump and output the first resonance frequency to the control circuit, and the control circuit identifies the change of state based on the first resonance frequency.

2. The negative pressure wound therapy device of claim 1, wherein the control circuit is further configured to receive a second temperature of the at least one piezoelectric pump detected by the temperature sensor subsequent to transmission of the second control signal, compare the second temperature to a second temperature threshold less than or equal to the first temperature threshold, and responsive to the second temperature being less than the second temperature threshold, transmit a third control signal to the at least one piezoelectric pump, the third control signal having a third RMS voltage equal to the first RMS voltage.

3. The negative pressure wound therapy device of claim 1, wherein the control circuit includes a timer, initiates the timer responsive to transmitting the first control signal, and identifies the expiration of the duration of time using the timer.

4. The negative pressure wound therapy device of claim 3, wherein the control circuit resets the timer responsive to transmitting the second control signal.

5. The negative pressure wound therapy device of claim 1, further comprising a pressure sensor configured to detect a first pressure of at least one of the piezoelectric pump or the wound site and output the first pressure to the control circuit, and the control circuit identifies the change of state responsive to comparing the first pressure to a target pressure and determining that the first pressure is greater than or equal to the target pressure.

6. The negative pressure wound therapy device of claim 5, wherein the control circuit is further configured to count a number of identifications of the at least one of the change of state or the expiration of the duration of time while the first pressure is less than the target pressure, compare the count to a count threshold, and responsive to determining that the count is greater than the count threshold, output a notification including at least one of a visual output or an audible output.

7. The negative pressure wound therapy device of claim 1, wherein the control circuit is coupled to the piezoelectric pump by an alternating current circuit having a first arm and a second arm, and the control circuit is configured to generate the first control signal to have the first RMS voltage by modulating a first phase angle of a first signal component associated with the first arm relative to a second phase angle of a second signal component associated with the second arm.

8. The negative pressure wound therapy device of claim 1, wherein the at least one of the change of state or the expiration of the duration of time is associated with overheating of the at least one piezoelectric pump.

9. The negative pressure wound therapy device of claim 1, wherein the control circuit generates the control signals as sine waves.

10. The negative pressure wound therapy device of claim 1, wherein the at least one piezoelectric pump includes at least a first piezoelectric pump and a second piezoelectric pump, wherein responsive to identifying the at least one of the change of state or the expiration of the duration of time, the control circuit transmits the second control signal to the first piezoelectric pump and transmits a third control signal having a third RMS voltage equal to the first RMS voltage to the second piezoelectric pump.

11. A method, comprising:
generating a first control signal having a first root mean square (RMS) voltage;
transmitting the first control signal to at least one piezoelectric pump configured to apply a vacuum to a wound site;
identifying at least one of a change of state of the at least one piezoelectric pump or an expiration of a duration of time associated with operation of the at least one piezoelectric pump;
responsive to identifying the at least one of the change of state or the expiration of the duration of time, generating a second control signal having a non-zero second RMS voltage less than the first RMS voltage;
transmitting the second control signal to the at least one piezoelectric pump;
receiving a first temperature of the at least one piezoelectric pump, wherein identifying the change includes comparing the first temperature to a first temperature threshold and determining that the first temperature is greater than the first temperature threshold; and
receiving a first resonance frequency of the at least one piezoelectric pump from a resonance detector and identifying the change of state based on the first resonance frequency.

12. The method of claim 11, further comprising initiating a timer responsive to transmitting the first control signal, and identifying the expiration of the duration of time using the timer.

13. The method of claim 11, further comprising generating the first control signal to have the first RMS voltage by modulating a first phase angle of a first signal component associated with a first arm of an alternating current circuit coupled to the at least one piezoelectric pump relative to a second phase angle of a second signal component associated with a second arm of the alternating current circuit.

14. A non-transitory computer readable medium storing computer executable instructions which when executed by a control circuit, cause the control circuit to perform a method comprising:
generating a first control signal having a first root mean square (RMS) voltage;
transmitting the first control signal to at least one piezoelectric pump configured to apply a vacuum to a wound site;
identifying at least one of a change of state of the at least one piezoelectric pump or an expiration of a duration of time associated with operation of the at least one piezoelectric pump;
responsive to identifying the at least one of the change of state or the expiration of the duration of time, generating a second control signal having a non-zero second RMS voltage less than the first RMS voltage; and
transmitting the second control signal to the at least one piezoelectric pump;
receiving a first temperature of the at least one piezoelectric pump, wherein identifying the change includes comparing the first temperature to a first temperature threshold and determining that the first temperature is greater than the first temperature threshold; and
receiving a first resonance frequency of the at least one piezoelectric pump from a resonance detector and identifying the change of state based on the first resonance frequency.

* * * * *